(12) United States Patent
Moles

(10) Patent No.: US 6,397,689 B1
(45) Date of Patent: Jun. 4, 2002

(54) SAMPLE PROBE

(75) Inventor: Donald R. Moles, Cedarville, OH (US)

(73) Assignee: YSI Incorporated, Yellow Springs, OH (US)

( * ) Notice: Subject to any disclaimer, the term of this patent is extended or adjusted under 35 U.S.C. 154(b) by 0 days.

(21) Appl. No.: 09/266,165

(22) Filed: Mar. 10, 1999

(51) Int. Cl.[7] .............................................. G01N 1/00
(52) U.S. Cl. ............................... 73/863.84; 73/863.23
(58) Field of Search .................... 73/863.23, 863.24, 73/863.81–863.84, 864.34, 864.35

(56) References Cited

U.S. PATENT DOCUMENTS

| | | | |
|---|---|---|---|
| 2,291,912 A | | 8/1942 | Meyers .......................... 103/44 |
| 3,039,309 A | * | 6/1962 | Vesper et al. ............... 73/863.83 |
| 3,048,121 A | | 8/1962 | Sheesley ...................... 103/152 |
| 3,101,619 A | * | 8/1963 | Hunter ....................... 73/863.84 |
| 3,318,251 A | | 5/1967 | Smith ............................. 103/49 |
| 3,526,223 A | | 9/1970 | Curtis ........................ 128/142.5 |
| 3,701,618 A | | 10/1972 | Wall et al. .................... 425/192 |
| 4,158,530 A | | 6/1979 | Bernstein ...................... 417/389 |
| 4,501,161 A | | 2/1985 | Endo et al. ................. 73/863.24 |
| 4,562,749 A | * | 1/1986 | Clark ......................... 73/863.84 |
| 4,683,207 A | | 7/1987 | Waarvik ........................ 435/311 |
| 4,755,111 A | | 7/1988 | Cocchi et al. ................ 417/394 |
| 4,782,817 A | | 11/1988 | Singh et al. .................... 600/17 |
| 5,163,909 A | | 11/1992 | Stewart ......................... 604/140 |
| 5,341,692 A | * | 8/1994 | Sher et al. ................. 73/864.63 |
| 5,736,654 A | * | 4/1998 | Dubois ....................... 73/863.84 |

FOREIGN PATENT DOCUMENTS

| | | |
|---|---|---|
| EP | 0455333 | 11/1991 |
| FR | 2647213 | 11/1990 |
| WO | 9840717 | 9/1998 |

OTHER PUBLICATIONS

PCT International Search Report; PCT Application No. PCT/US00/06483; filed on Oct. 3, 2000.

Written Opinion issued in corresponding International Application No. PCT/US00/06483 (issued Jan. 11, 2001).

* cited by examiner

Primary Examiner—Robert Raevis
(74) Attorney, Agent, or Firm—Thompson Hine LLP

(57) ABSTRACT

A sampling probe for withdrawing and filtering a portion of material from a vessel having an inner chamber containing the material and a port for receiving a probe. The sampling probe comprises a casing having a sample inlet, a pumping chamber having a pump for drawing a portion of the material into the pumping chamber through the sample inlet, and a filter chamber downstream of the pumping chamber. The filter chamber includes a filter which divides the filter chamber into a retentate portion and a filtrate portion, wherein at least part of the withdrawn material passes through the filter into the filtrate portion.

18 Claims, 5 Drawing Sheets

SAMPLE PROBE

The present invention is directed to a sampling probe for filtering fluid contained in a vessel, and more particularly, to a sampling probe for filtering fluid contained in a vessel, wherein the sampling probe is shaped to be received within an inner chamber of the vessel.

BACKGROUND OF THE INVENTION

In the bio-processing, pharmaceutical or other related industries, a liquid broth containing cells, fermentation materials, bacteria, cell cultures or other microorganisms may be formed during manufacturing processes. The broth must be periodically checked to monitor the level of certain compositions or byproducts in the broth, such as nutrient waste groups of small molecules, protein concentrations, or other compounds. The broth is typically contained in a large vessel that has a port formed in its top or side, and the port is shaped to receive a probe therethrough for withdrawing a sample of the broth. Typically, the size of the port is set at an industry standard, such as, in one case, a diameter of about 12 mm.

In order to draw a sample from the broth, a generally tube-shaped probe is typically passed through the port in the vessel until one end of the probe is submerged in the broth. A sample of broth is then drawn up through the straw-like probe. A peristaltic or other pump may be used to draw the sample up the probe and out of the vessel. Once the sample is obtained, it is passed through a separate tangential filter element to filter out the cells. In many cases, a second pump is used to draw the broth through the filter element. The filtered fluid may then be analyzed for certain levels of components or byproducts, such as glucose, lactate, amino acids, ammonia, glycerol, etc. The unfiltered portion of the withdrawn broth is returned to the vessel via another dip tube.

There are several drawbacks in the prior art methods for withdrawing a sample. For example, it is desirable to return the unfiltered broth to the vessel. However, in practice, most technicians will not return the unfiltered sample to the broth in order to minimize the possibility of contaminating the broth. When a sample is removed from the vessel, it is felt that returning the sample to the broth risks contaminating the broth. Furthermore, most prior art methods draw a relatively high "hold-up" volume; that is, a relatively large volume of sampled fluid is removed from the broth. Thus, the relatively high volume withdrawal sample becomes wasted fluid when it is not returned to the broth.

The prior art sampling systems may draw the fluid through a filter element by means of a pump. However, this may cause air to be entrained out of fluid after it is filtered. The bubbles may conglomerate and lock together to block flow through the filter line. Furthermore, precise volumetric measurements are required in analyzing the sample, and entrained air can also thereby cause inaccurate volumetric measurements of the broth. Finally, the prior art designs are vulnerable to contamination and because they require separate pumping and filter apparatuses, and are often bulky and expensive.

Accordingly, there exists a need for a sampling probe which has a low hold-up volume, reduces the entrainment of air, reduces the risk of contamination and is relatively small and inexpensive for easy disposability.

SUMMARY OF INVENTION

The present invention is a sampling probe for sampling and filtering a portion of material that has a relatively small hold-up volume, reduces the entrainment of air, and is compact and inexpensive. The sampling probe incorporates a pump and a filter into one assembly, and can be accepted into a standard sized port formed in a vessel. Because the probe is inexpensive, it may be disposed of after a single use, which eliminates the possibility of contamination from previous uses. In one embodiment, the invention is a sampling probe for withdrawing and filtering a portion of material from a vessel having an inner chamber containing the material and a port for receiving a probe. The sampling probe comprises a casing having a sample inlet, a pumping chamber having a pump for drawing a portion of the material into the pumping chamber through the sample inlet, and a filter chamber downstream of the pumping chamber. The filter chamber includes a filter which divides the filter chamber into a retentate portion and a filtrate portion, wherein at least part of the withdrawn material passes through the filter into the filtrate portion.

Other objects and advantages of the present invention will become apparent from the following description, the accompanying drawings and the appended claims.

DETAILED DESCRIPTION

Figure 1:
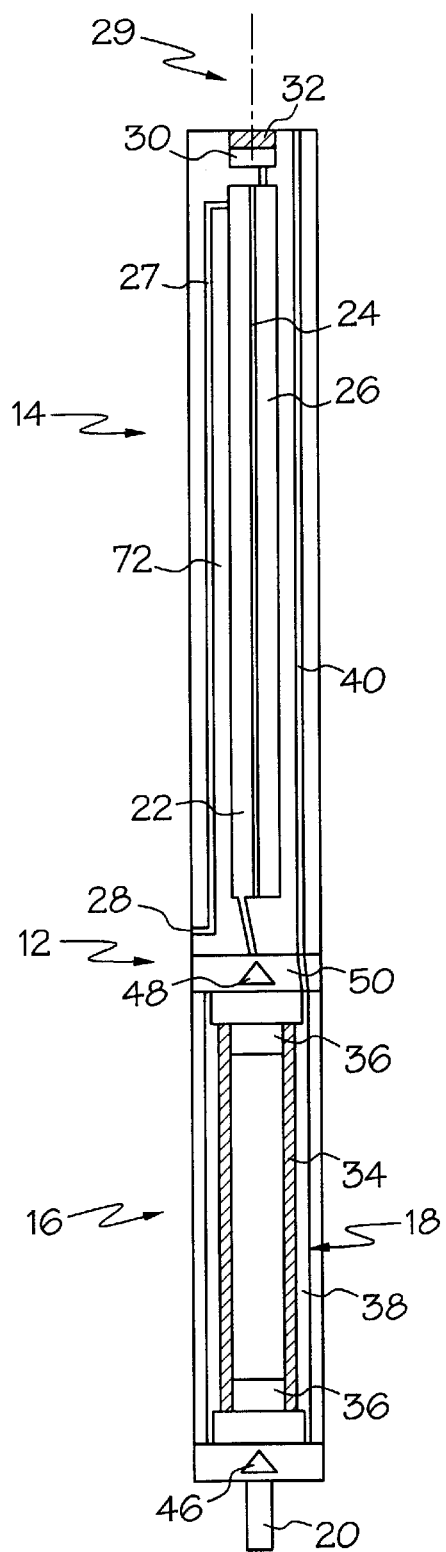
FIG. 1 is a side cross sectional view of one embodiment of the sampling probe of the present invention, with the pump in the relaxed position.

The sampling probe of the present invention is shown in FIGS. 1–5, and is first described in general overview. The sampling probe 10 includes an outer casing 12 that includes a filter body 14 and a pump body 16. A pump 18 is contained within the pump body 16, and draws fluid into the sampling probe 10 through the sample inlet 20. After passing through the pump 18, the fluid enters the filter body 14 at the retentate chamber 22. Part of the fluid in the retentate chamber 22 passes through the filter 24 into the filtrate chamber 26. The unfiltered fluid remains in the retentate chamber 22 and exits at the retentate outlet 28. The filtered fluid is urged to the top of the filtrate chamber 26 into the sampling chamber 30. The filtered fluid is then passed through a syringe needle 29 that is passed through the through the septa 32 into the sampling chamber 30. Fluid passing through the syringe needle 29 may then be analyzed by an analyzer. Microfluidic, non-microfluidic, and other types of analyzers may be used. For example, a 2700 Chemistry Analyzer manufactured by YSI Incorporated of Yellow Springs, Ohio may be utilized. Only a portion of the syringe needle 29 is shown, as the other end is connected to an analyzer or the like.

It should be noted that the terms "upstream" and "downstream" are used herein to signify directions of the fluid flow, with an upstream location being closer to the inlet in the fluid flow path relative to a downstream location.

However, at some points in drawings of the sampling probe, the downstream direction is actually in the "up" direction, and vice versa.

Figure 2:
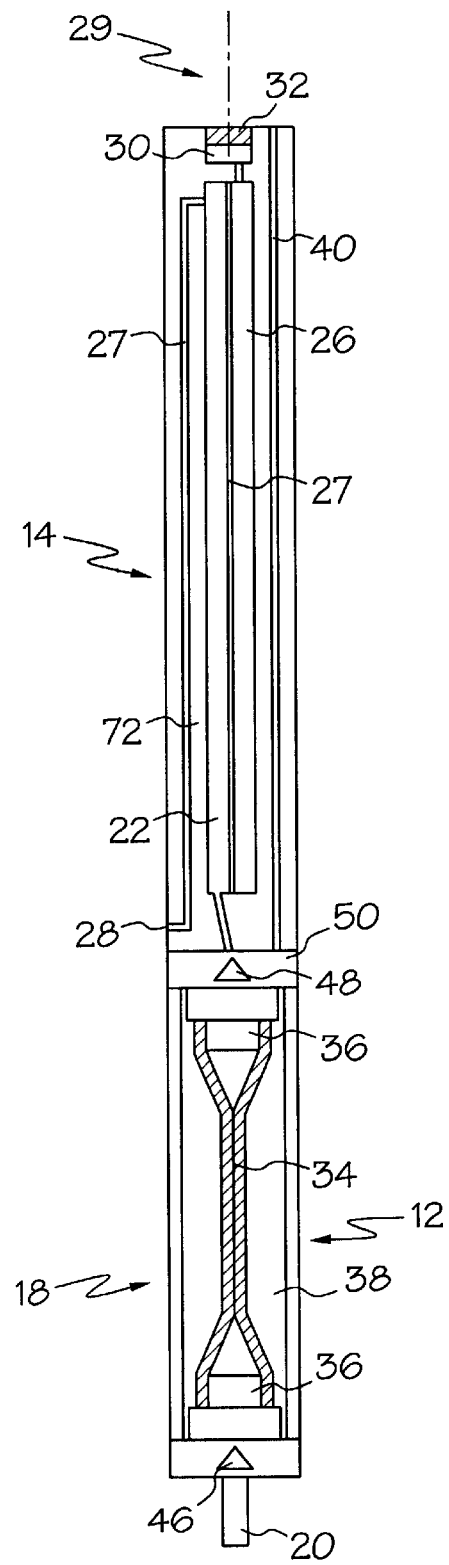
FIG. 2 is a side cross sectional view of the sampling probe of FIG. 1, with the pump in the collapsed position.

As shown in FIGS. 1–2, the sampling probe 10 includes a pump 18 that utilizes a generally cylindrical pump bladder 34. The pump bladder 34 is generally cylindrical, and may be made from a resilient, bio-compatible material such as silicone rubber: The pump bladder 34 is fit over a pair of bladder barbs 36 at each of its ends. However, the pump 18 may take other forms, as will be discussed in greater detail below. A fluid chamber 38 surrounds the pump bladder 34 and is coupled to a fluid tube 40 that extends through the filter body 14. Typically, the pump 18 is actuated using compressed air, but a hydraulic fluid could also be used. The invention will be hereafter be described with the use of compressed air to activate the pump.

Figure 5:
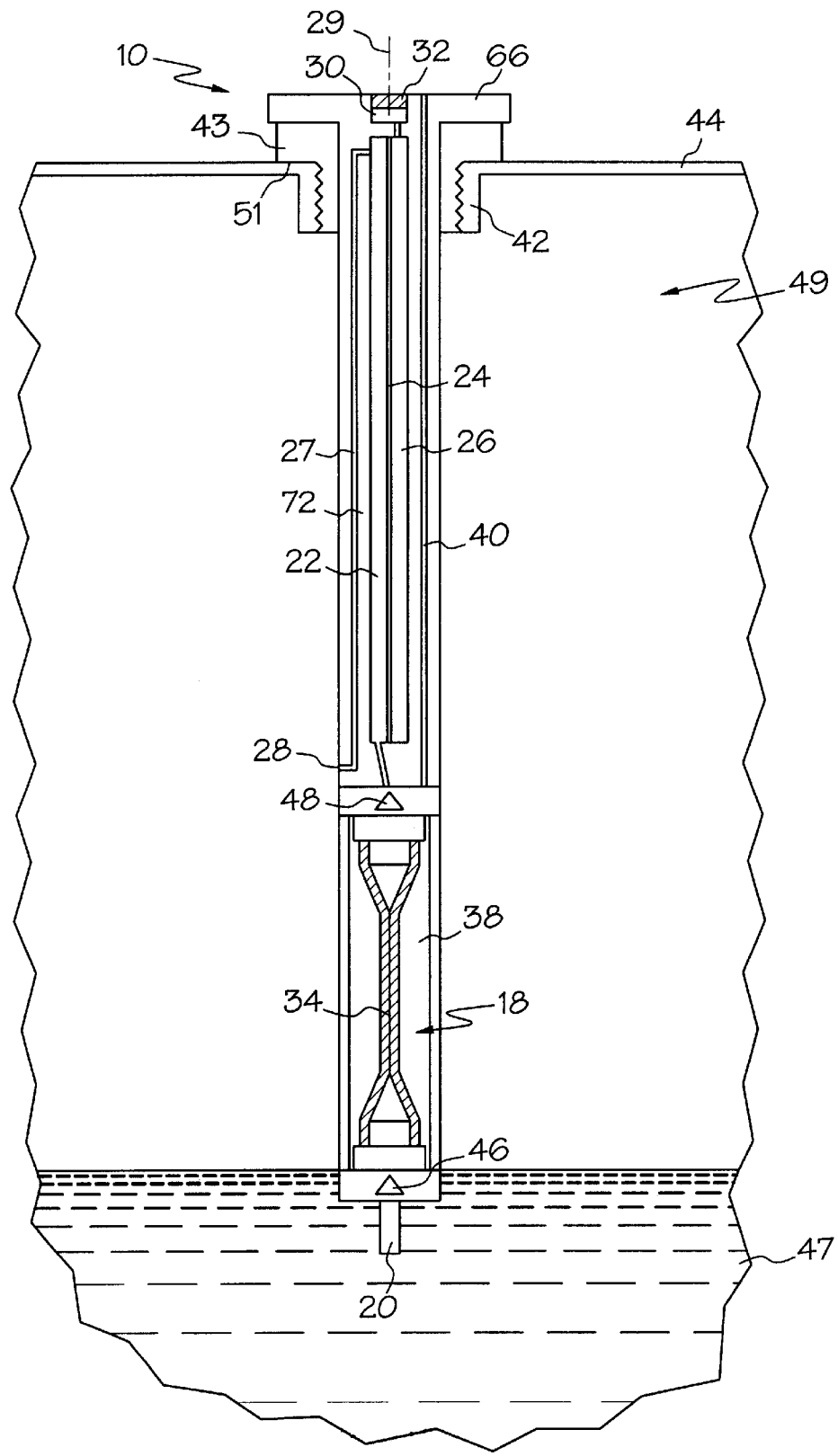
FIG. 5 is a side, cross sectional view of the sampling probe of the present invention, shown received in a vessel port.

In operation, the sampling probe 10 is inserted into a threaded port 42 in a vessel 44 that contains fluid 47 to be sampled (FIG. 5). The vessel 44 has an inner chamber 49 containing the fluid 47, and the probe 10 is urged into the port 42 until the probe inlet 20 is submerged in the fluid 47. The pump 18 then pumps fluid 47 into the sampling probe 10 by contraction and relaxation of the pump bladder 34. The pump bladder 34 is shown in FIG. 1 in its relaxed position, and in FIGS. 2 and 5 in its collapsed position. In order to attain the collapsed position, compressed air is passed through the tube 40 into the chamber 38, and the resultant increase in pressure causes the bladder 34 to collapse. In order to return to the relaxed position, the flow of compressed air through the tube 40 is terminated, and excess air is vented from the chamber 38, for example through the tube 40. The pump bladder 34, through its natural resiliency, returns to the relaxed position as the air is vented. Alternately, in order to return the pump bladder 34 to the relaxed position, a negative pressure may be created in the chamber 38 through the path 40, thereby causing the pump bladder 34 to retract at an even faster rate. As the pump bladder 34 returns to its un-collapsed position, the pressure differential causes the inlet check valve 46 to open, the outlet check valve 48 to close, and fluid 47 is drawn through the probe inlet 20 into the pump bladder 34. Once sufficient fluid has entered the pump bladder 34, compressed air is then passed through the tube 40 and into the chamber 38. This change in pressure causes the inlet check valve 46 to close and the outlet check valve 48 to open, and forces fluid in the pump bladder 34 into the retentate chamber 22 via the check valve 48. Continued contractions of the pump bladder 34 continue to feed fluid into the retentate chamber 22. This type of pump is termed a pneumastaltic pump. In one embodiment, the pump bladder is about 3" long, has an outer diameter of about 5/16", and an inner diameter of about 3/16".

In an alternate embodiment, the internal cavity in the pump bladder 34 may be alternately filled and emptied with compressed air, which displaces the fluid that is surrounding the pump bladder 34. In this embodiment the pump bladder 34 may take the form of a closed-end tube in communication with the compressed air tube 40. In this case the incoming fluid enters the chamber 38 surrounding the pump bladder 34 via inlet check valve 46. When the pump bladder 38 is expanded, the fluid in the chamber 38 is displaced out of the chamber 38, and exits through the outlet check valve 48. Of course, various other pumping methods may be used without departing from the scope of the present invention.

The pneumastaltic pump 18 forces the withdrawn fluid into the retentate chamber 22. Due to the pressure of the fluid in the retentate chamber 22, part of the fluid in the retentate chamber 22 is forced through the filter sheet 24, and into the filtrate chamber 26. The filter sheet 24 filters out any cells or other relatively large bodies, and is in one embodiment a microporous polyether sulfone. In one embodiment the filter sheet or membrane 24 is about 5" long and about ½" wide, and has a pore size ranging from about 0.05 microns to about 1 micron. The tangential flow across the filter sheet 24 is advantageous because it does not force all fluid through the filter sheet 24, and thereby avoids clogging of the filter sheet 24. Any cells or other structures that accumulate along the filter surface may be washed downstream by the fluid flowing through the retentate chamber 22. Thus, tangential cross flows across the filter sheet 24 maintain the permeability of the filter sheet 24 by preventing a buildup of materials on its surface. The filtered fluid in the filtrate chamber 26 eventually works its way to the top of the filtrate chamber 26, and into the sampling chamber 30. There, the sampled fluid is urged through the syringe 29 and into an analyzer.

The unfiltered fluid in the retentate chamber 22 is forced to the top of the retentate chamber 22 and back down through the filter body 14 via the retentate exit path 27. Ultimately, the unfiltered fluid exits at the retentate outlet 28, and may be returned to the vessel inner chamber 49. Fluid exiting the outlet 28 trickles down the side of the pump body 16, and is returned to the fluid source 47. The retentate outlet 28 provides an automatic return path for the unfiltered fluid to the fluid source 47.

Figure 3:
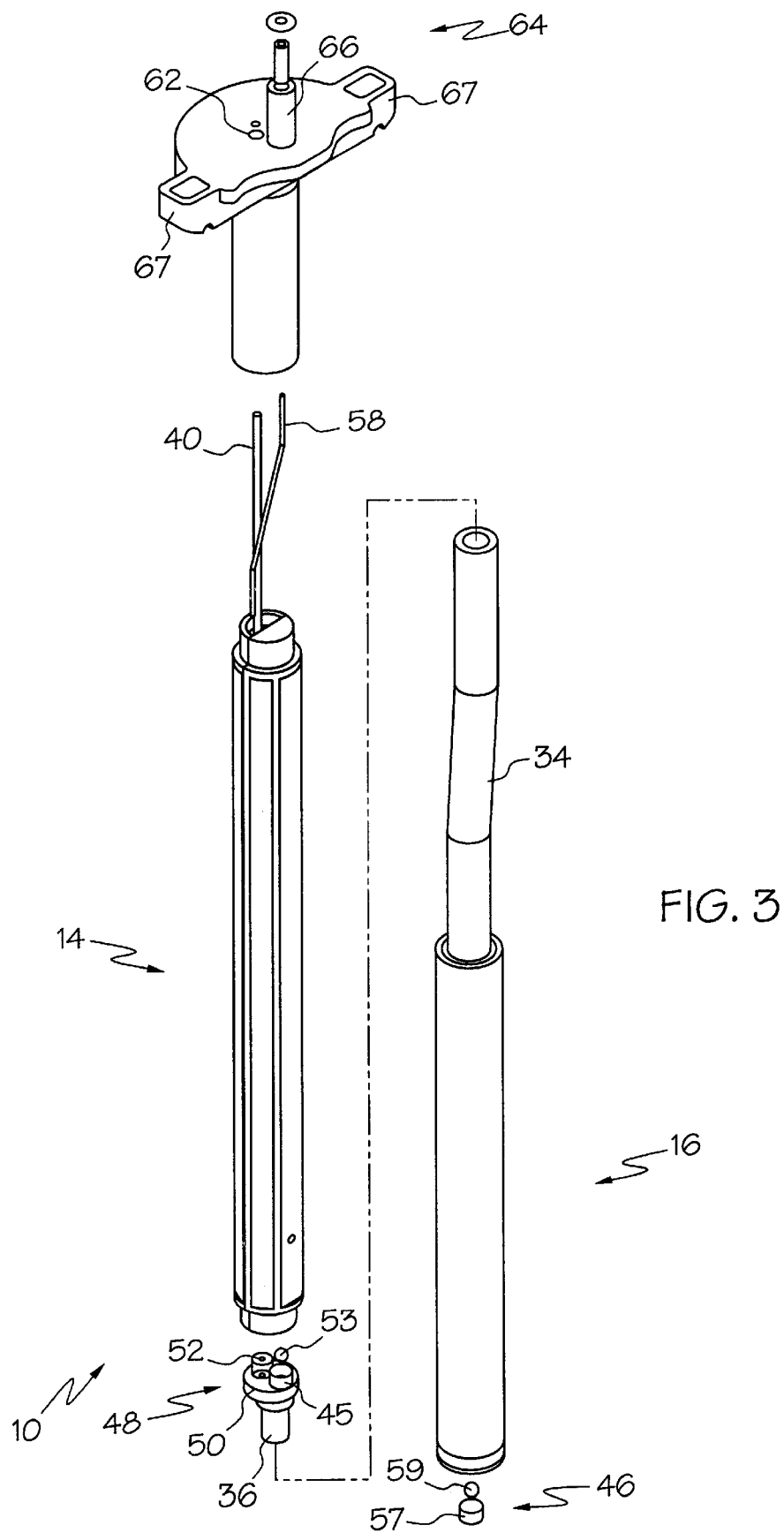
FIG. 3 is an exploded, perspective view of one embodiment of the sampling probe of the present invention.
Figure 4:
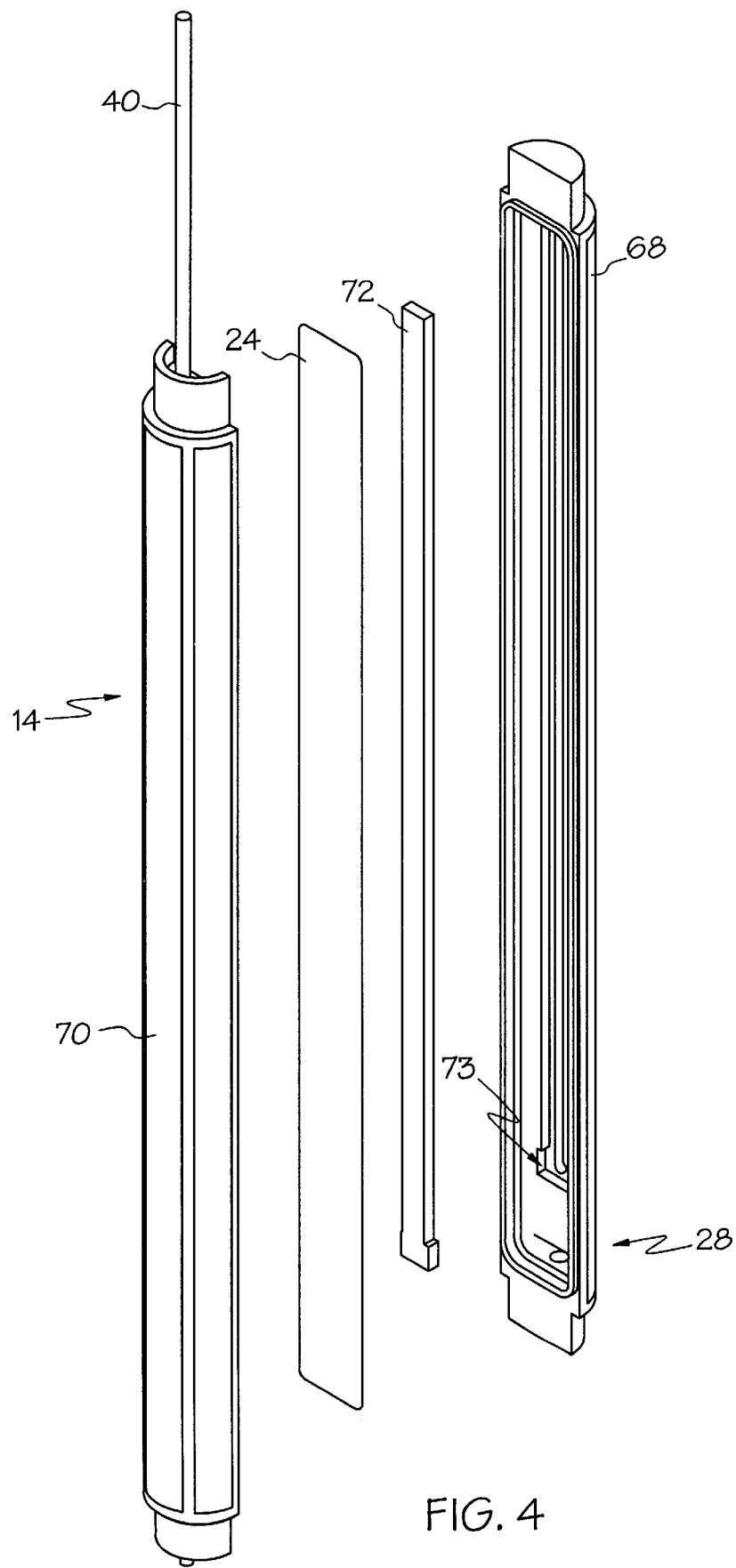
FIG. 4 is an exploded view of the filter body of the sampling probe of FIG. 3.

FIGS. 3–4 show a preferred embodiment of the sampling probe of the present invention. The exploded view shows the pump body 16 removed from the filter body 14, an outlet check valve 48 disposed between the filter body 14 and the pump body 16, and an inlet check valve 46 at the bottom of the pump body. The outlet check valve 48 includes a cup 45 that receives a ball 53, and the inlet check valve 46 includes a cup 57 that similarly receives a ball 59. The outlet check valve 48 is located within a plug 50, which also has a port 52 for coupling the tube 40 to the chamber 38. It should be noted that instead of being formed as discreet parts, the plug 50, inlet check valve 46 and outlet check valve 48 may be integrally molded as part of the pump body 16 and/or filter body 14. Similarly, the tube 40 may be formed as an integral channel in the filter body 14.

The filtrate tube 58 guides filtered fluid from the filtrate chamber 26 to the sampling chamber 30. A to piece 64 fits over the filter body 14 and has a pair of flanges 67 to support the sampling probe 10 in the port 42 during sampling operations. The top piece 64 carries the compressed air inlet 62 (which is in fluid communication with the tube 40) and the syringe inlet 66.

Figure 6:
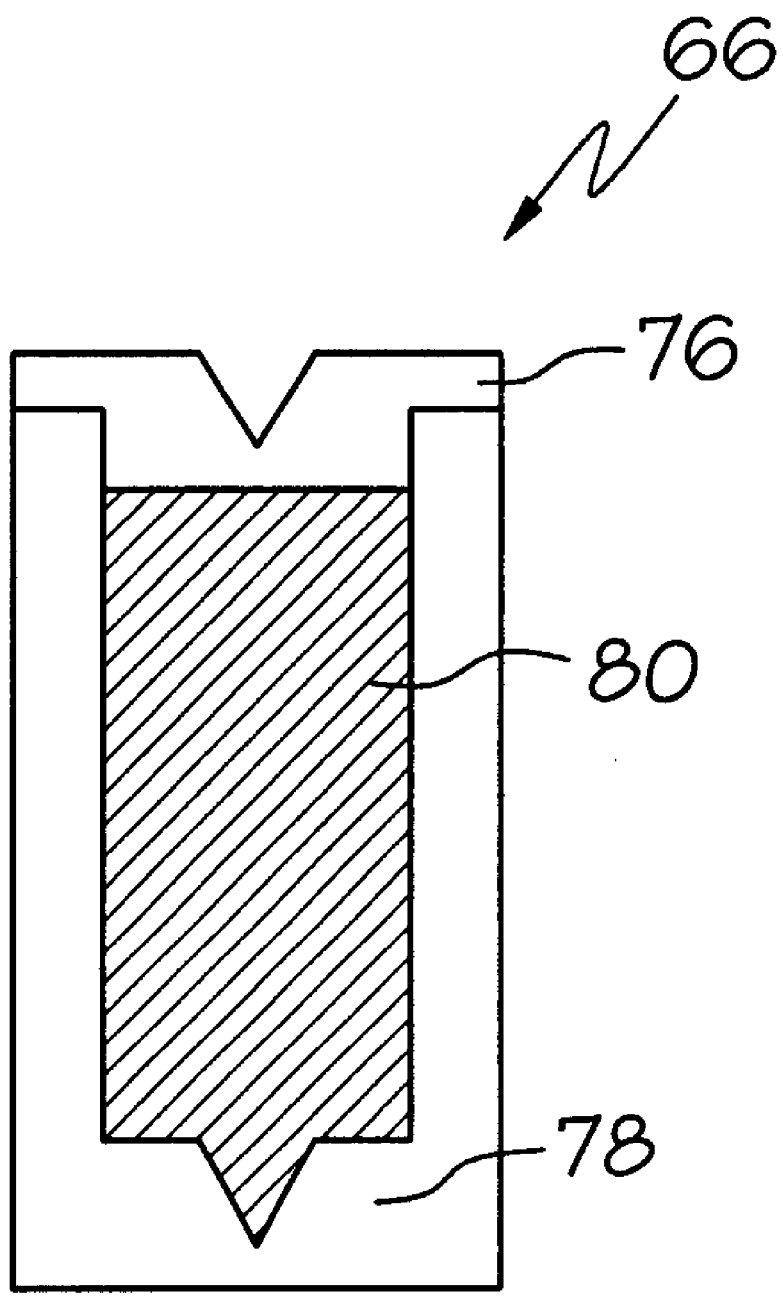
FIG. 6 is a side, cross sectional view of a syringe inlet used in the sampling probe of the present invention.

In a preferred embodiment, the syringe inlet 66 is a self-sterilizing syringe inlet 66 shown in FIG. 6. The syringe inlet 66 is preferably used in place of the septa 32 of FIGS. 1, 2 and 5. The inlet 66 includes an upper membrane 76 and a lower membrane 78 defining a steriliant cavity 80 therebetween. The cavity 80 is filled with a chemical steriliant which sterilizes a syringe needle passed through the syringe inlet 66 to withdraw fluid from the sampling chamber 30. In a preferred embodiment, when a syringe needle is passed through the inlet 66, the tip of the needle resides in the steriliant cavity 80 for a predetermined length of time. This ensures that the needle is properly sterilized, and also allows the steriliant fluid to enter the needle such that both the inner and outer diameters of the needle are sterilized. The self sterilizing inlet 66 helps to prevent contamination of the filtered fluid, and preserves the sterility of the filtrate conduits.

FIG. 4 shows an exploded view of the filter body 14. The outer casing of the filter body 14 includes two opposed body halves 68, 70, and the filter sheet or membrane 24 is disposed therebetween. A backing plate 72 is received in the filter plate cut-out 73 in the filter body half 68. As best shown in FIGS. 1–2, the backing plate 72 defines the retentate chamber 22 and exit path 27.

As shown in FIG. 5, the sampling probe 10 of the present invention is sized so as to fit within the threaded port 42 in the vessel. Thus, both the pump 18 and the filter 24 are located within the inner chamber 49 of the vessel. Accordingly, the volume of sampled fluid may be small, and the pumping and filtering operations are carried out in the inner chamber 49 of the vessel 44. This avoids having to remove fluid from the vessel 44, and returning the fluid to the vessel. Because the returned fluid never leaves the vessel 44, the chances of contamination are reduced. In this manner, the probe of the present invention provides access to the filtered fluid without transporting significant fluid volumes outside the vessel 44. The pump 18 and filter 24 are located adjacent the fluid source 47, and therefore the distance which the fluid must travel before reaching the sampling chamber 30 is minimal. This, in combination with the low hold-up volume, reduces the response time of the sampling probe. That is, the time required to move fluid from the fluid source 47 to the sampling chamber 30 for removal and examination is reduced.

In one embodiment shown in FIG. 5, the probe 10 is passed through a threaded nut 43 that is received in the threaded port 42 of the vessel 44. The threaded nut 43 has an inner diameter sized to closely receive the casing 12 of the probe 10 therein, and an upper surface to support the flanges 67 thereon. The threaded nut 43 preferably includes at least one seal or O-ring on its inner surface (not shown) to seal the portion of the probe inside the chamber 49 relative the surrounding atmosphere. The threaded nut 43 also preferably includes seals on its lower surface 51 to seal the inner chamber 49 relative the surrounding atmosphere. Various sizes and shapes of the threaded nut 43 may be used in the industry, and typically the nut 43 is comprised of several separate components that are not shown. The various components help to form effective seals for the probe 10 and inner chamber 49 relative the surrounding atmosphere, and the specific form and shape of the threaded nut is not critical to the present invention.

The sampling probe of the present invention is relatively small and may be manufactured of relatively inexpensive materials, and thereby may be easily disposed of and replaced. Thus, a separate probe may be used for each separate batch of broth that is prepared. This helps to reduce the changes of "carryover" contamination; that is, the chances of trace elements of an earlier batch appearing in and contaminating a subsequent batch are reduced. The present invention also combines the pump and filter systems into a single sampling probe apparatus, which helps to increase the robustness of the system and reduce its complexity.

A further advantage is provided by the primarily "pushing" pumping force of the present invention. As described earlier, the fluid in the sampling probe 10 is urged downstream by the contraction of the pump 18, which urges fluid out of the pump bladder 34 and into the retentate chamber. This, in turn, urges fluid already in the retentate chamber 22 further downstream through the system and ultimately out of the retentate outlet 28. Accordingly, the fluid is "pushed" downstream by fluid exiting the pump bladder 34. This is to be contrasted with the prior art systems, which often "pull" fluid by creating a reduced pressure downstream of the fluid. Thus the present invention reduces the problems of entrained air noted earlier.

The present design allows the pump 18 to be located inside the probe, and thus essentially inside the vessel 44, while the driving force, i.e., the source of compressed gas or hydraulic fluid (not shown), is located remotely from the pump. Furthermore, because in one embodiment the probe is preferably not coupled to a source of mechanical energy outside the probe (i.e. a mechanical pump coupled to the probe by rotating shafts or the like), the need for seals is greatly reduced. It is known that seal failure may be a source for contamination of the fluid.

While the forms of the apparatus described herein constitute a preferred embodiment of the invention, the present invention is not limited to the precise forms described herein, and changes may be made therein without departing from the scope of the invention.

What is claimed is:

1. A sampling probe for filtering a portion of fluid contained in a vessel having an inner chamber containing said fluid and a port for receiving a probe, the sampling probe comprising:
   a casing having a sample inlet;
   a pumping chamber having a pump for drawing a portion of said fluid into said pumping chamber through said sample inlet; and
   a filter chamber downstream of said pumping chamber, said filter chamber including a filter which divides said filter chamber into a retentate portion and a filtrate portion, wherein at least part of said withdrawn fluid passes through said filter into said filtrate portion wherein said pumping chamber and said filter chamber are received in a casing, and wherein said casing is shaped to be passed through said port and be received in said inner chamber such that said filter chamber is generally received in said inner chamber.

2. The sampling probe of claim 1 wherein said pump is powered by a source of compressed fluid.

3. The sampling probe of claim 1 further comprising a sampling chamber for receiving at least part of the filtered fluid, said sampling chamber being located such that said filtered fluid may be located adjacent an outer edge of said vessel and removed from said sampling chamber.

4. The sampling probe of claim 3 wherein said sampling chamber includes a septa through which a needle may be passed to receive said filtered fluid.

5. The sampling probe of claim 4 wherein said septa includes an outer membrane and an inner membrane defining a cavity therebetween.

6. The sampling probe of claim 5 wherein said cavity may receive a fluid therein which sterilizes said needle when said needle is passed through said septa.

7. The sampling probe of claim 5 wherein said cavity includes a fluid therein which sterilizes said needle when said needle is passed through said septa.

8. The sampling probe of claim 1 further comprising a return path for returning at least part of said withdrawn fluid to said inner chamber.

9. The sampling probe of claim 1 further comprising a return path for returning the unfiltered part of said withdrawn fluid to said inner chamber.

10. The sampling probe of claim 1 wherein said withdrawn fluid flows across said filter under pressure in said filter chamber h that at least part of said withdrawn fluid passes through said filter.

11. The sampling probe of claim 1 wherein said pump is a pneumastaltic pump.

12. The sampling probe of claim 1 wherein said pump is a powered by compressed fluid.

13. The sampling probe of claim 1 wherein said pump is a generally flexible bladder for receiving said withdrawn fluid therein.

14. The sampling probe of claim 1 wherein said probe fits in said port to seal said inner chamber relative the surrounding atmosphere.

15. The sampling probe of claim 1 further comprising an inlet check valve adjacent said sample inlet, and an outlet check valve between said pumping chamber and said filter chamber.

16. The sampling probe of claim 1 further comprising a fluid line located inside said casing and coupled to said pumping chamber to supply a fluid to said pumping chamber to operate said pump.

17. A method for filtering a portion of fluid contained in a vessel having an inner chamber containing said fluid and a port for receiving a probe, the method comprising:
   providing a sampling probe comprising a pump contained in a pump chamber within a casing for withdrawing a portion of said fluid into said pump chamber, and a filter located in said casing and downstream of said pump for filtering at least part of the withdrawn fluid;
   passing said sampling probe through said port such that said filter is generally located inside said vessel and at least part of said probe is received in said fluid; and
   causing said pump to withdraw and filter a portion of said fluid.

18. The method of claim 17 further comprising the steps of supplying said filtered portion of said fluid to a sampling chamber, and passing said filtered portion through a needle received in said sampling chamber.

* * * * *